United States Patent
Hrboticka et al.

(10) Patent No.: US 9,068,951 B2
(45) Date of Patent: Jun. 30, 2015

(54) TESTER FOR PEROXIDE-BASED COMPOUNDS

(71) Applicant: Precision Laboratories, Inc., Cottonwood, AZ (US)

(72) Inventors: Eva Hrboticka, Brno (CZ); James A Bertsch, Pittsford, NY (US)

(73) Assignee: PRECISION LABORATORIES, INC., Cottonwood, AZ (US)

( * ) Notice: Subject to any disclaimer, the term of this patent is extended or adjusted under 35 U.S.C. 154(b) by 0 days.

(21) Appl. No.: 14/021,158

(22) Filed: Sep. 9, 2013

(65) Prior Publication Data
US 2015/0072435 A1 Mar. 12, 2015

(51) Int. Cl.
*G01N 21/78* (2006.01)
*G01N 21/77* (2006.01)
*G01N 21/00* (2006.01)
*G01N 33/00* (2006.01)

(52) U.S. Cl.
CPC ............ *G01N 21/78* (2013.01); *G01N 33/0036* (2013.01); *Y10T 436/12* (2015.01)

(58) Field of Classification Search
CPC ..... G01N 21/783; G01N 21/78; G01N 21/77; G01N 21/00; G01N 33/0036; G01N 33/0057; G01N 33/0027; G01N 33/0009; G01N 33/00; Y10T 436/00; Y10T 436/12
USPC ........... 436/135, 127; 422/83, 50, 82.05, 68.1
See application file for complete search history.

(56) References Cited

U.S. PATENT DOCUMENTS

| | | | | |
|---|---|---|---|---|
| 4,452,887 A * | 6/1984 | Kitajima et al. | ................. | 435/14 |
| 5,200,321 A * | 4/1993 | Kidwell | .......................... | 435/7.9 |
| 5,393,493 A * | 2/1995 | Makino et al. | ................. | 422/422 |
| 5,420,016 A * | 5/1995 | Boguslaski et al. | ............ | 435/12 |
| 7,713,474 B2 * | 5/2010 | Schulman et al. | ............. | 422/421 |
| 7,829,020 B2 * | 11/2010 | Pagoria et al. | ................. | 422/402 |
| 2003/0215358 A1 * | 11/2003 | Schulman et al. | .............. | 422/56 |
| 2005/0180879 A1 * | 8/2005 | Hrboticka | ....................... | 422/56 |

* cited by examiner

*Primary Examiner* — Christine T Mui
(74) *Attorney, Agent, or Firm* — Ladas & Parry LLP

(57) ABSTRACT

An apparatus and a method for the colorimetric detection testing of peroxide-based compositions is disclosed. The apparatus comprises a first carrier having an acidic compound in dry form for hydrolysis of peroxide-based compounds and a second carrier having a colorimetric detection reagent composition in dry form. The carriers are positioned with respect to a support member to facilitate transfer of a solution containing a peroxide-based compound hydrolyzed by the acidic compound when activated into contact with the reagent composition of the second carrier for observation of any resulting color indication. The method comprises steps of applying the acidic compound and colorimetric detection reagent composition is liquid forms to the respective carriers and allowing the applied formulations to dry. The carriers are then positioned with respect to a tester support member to facilitate transfer of a solution containing a peroxide-based compound hydrolyzed by the acidic compound when activated into contact with the reagent composition of the second carrier for observation of any resulting color indication. When a test is to be performed the formulations are activated by water, and a composition to be tested is placed in contact with the carriers and any color change of the colorimetric detection reagent is observed.

14 Claims, 3 Drawing Sheets

TESTER FOR PEROXIDE-BASED COMPOUNDS

The present invention is directed to a new and improved system for detection of the presence of peroxide-based compounds. The detection of such compounds is of particular value for detecting explosive formulations.

BACKGROUND OF THE INVENTION

The recent past has shown an upsurge in the use of peroxide-based explosives. Terrorist organizations, in particular, have shown an affinity for the use of such explosives, as they can be made from relatively easily obtained components and are simple and inexpensive to fabricate. The 2005 attacks on the London transit system, for example, used peroxide-based explosives. The attempted bombing of a Northwest Airlines airliner in 2009 used a TATP (triacetone triperoxide) explosive. As peroxide-based explosives do not normally include nitro groups, do not exhibit UV absorbance or fluorescence and do not provide easy ionization, many conventional tests for explosive components cannot be used for their detection. Accordingly there is an increased need for methods and systems for providing fast and accurate testing for the presence of such compounds, and especially for such testers that can be used in a field environment.

U.S. Pat. No. 6,767,717 of Jul. 27, 1994 to Itzhaky et al is directed to a method for detecting peroxide-based explosives which comprises dissolving a sample of the material to be tested in a suitable organic solvent, contacting the solution with a solution of a strong acid to release hydrogen peroxide, and contacting the resulting mixture with a peroxidase enzyme, a buffer and a substrate capable of being oxidized in a manner that permits a physical change of the substrate to be observed.

International Patent publication of Sep. 29, 2005, No. WO 2005/089058 of Amisar is directed to a method and kit for detecting explosive substances containing chlorate, bromate and/or organic peroxide. The suspect substance is contacted with a strongly acid solution of at least one primary or secondary aromatic amine. A chlorate or bromate type of explosive provides a distinct coloration. In the absence of such coloration, the same sample is contacted with a solution comprising cations of at least one transition metal. Organic peroxide in the sample, which was at least partially hydrolyzed by the strong acid, affords a distinct coloration.

WO 99/43846 sets forth a method and kit for detecting an organic peroxide-based explosive in a sample. The sample is dissolved in a suitable organic solvent and then hydrolyzed with a strong acid to release hydrogen peroxide, which is then detected in a known manner.

U.S. Pat. No. 7,829,020 of Jul. 31, 2008 to Pagoria et al. discloses a field-portable colorimetric detection device for organic peroxides and hydrogen peroxides. It utilizes a swipe material attached to a polyethylene tube containing two crushable vials containing components of a colorimetric detection reagent, separated into dry and liquid ingredients. After swiping a suspected substance or surface the vials are broken, the ingredients are is mixed thoroughly, and the reagent is allowed to wick into the swipe material. The presence of organic peroxides or hydrogen peroxide is confirmed by a deep blue color. The colorimetric reagent components have to remain separated before a test is performed because of high instability. When mixed together they themselves can develop a blue color (false positive blank) after about a week.

BRIEF DESCRIPTION OF THE INVENTION

The present invention provides a simple and effective system for the colorimetric detection of organic peroxides and hydrogen peroxide, utilizing a tester based completely on "dry reagent chemistry" for detecting an organic peroxide, for example peroxide-based explosives such TATP and hexamethylene triperoxidediamine (HMTD). The tester comprises a strong acid capable of decomposing a peroxide-based compound and releasing in situ a final analyte, hydrogen peroxide, for a colorimetric reaction. The tester comprises all necessary reagents in dry stable form, thus avoiding the need for crushable ampoules and/or harmful liquids or dispensers. The reagent system is activated with water just before use. The tester is compact, may be easily transported and handled as it does not contain harmful liquid reagents, such as sulfuric or hydrochloric acid, requiring special transportation conditions and safety precautions during handling, and can be safely used anywhere as a primary screening tool by non-technical persons.

BRIEF DESCRIPTION OF THE DRAWINGS

A fuller understanding of the present invention will be obtained upon review of the following detailed description of illustrative embodiments thereof, in conjunction with the accompanying drawings, wherein.

DETAILED DESCRIPTION OF THE INVENTION

Figure 1:
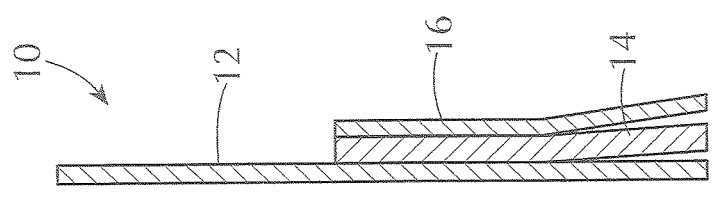
FIGS. 1 and 2 are side elevation representations of two forms of a first general embodiment of a tester constructed in accordance with the present invention.

The compact dry reagent chemistry-based tester of the present invention comprises all necessary reagents for generating and releasing hydrogen peroxide as an analyte and the colorimetric detection thereof in one integral analytical element. With initial reference to FIG. 1, tester 10 comprises a support member 12 which carries first and second absorbent/adsorbent substrate carrier matrices 14 and 16 which together carry a reagent system capable of generating a detectable response to the hydrogen peroxide analyte developed. The support member 12 is of an elongated construction, allowing the distal (upper) end to serve as a handle, avoiding user contact with the carriers or test solution. The support member may be fabricated from any of a wide range of materials. Typical materials suitable for the support member include various plastics, such as polypropylene, polystyrene, polycarbonates, and polyethylene terephthalate. Suitable materials forming the carriers 14 and 16 include bibulous materials, such as filter or chromatographic paper, nonwoven and woven fabrics, gel foams, synthetic fleeces, glass fibers, hydrophilic polymer sheets and other otherwise suitable, inert porous materials well known in the art.

One of the carriers, carrier 14, contains a strongly acidic compound for hydrolysis of peroxide-based compounds in the tested sample, which releases hydrogen peroxide as a real analyte. The strongly acidic compound is incorporated in the carrier in dry stable form, and may be chosen from solid organic acids, such as citric acid, oxalic acid, tartaric acid or metaphosphoric acid, as well as from strongly acidic polyelectrolyte polymers, such as poly(vinylsulfuric acid), poly (styrene sulfonic acid) or maleic anhydride/methylvinyl ether copolymers. One or more of such acidic compounds may be incorporated into the carrier in suitable quantities. Citric acid, in concentrations of from 5-70 percent, and more particularly 25-35 percent may be particularly preferred. An appropriate solution of the acidic compound is prepared, the carrier dipped or otherwise saturated with the solution, and allowed to dry.

The second carrier, carrier 16, provides the reagents for colorimetric detection of the in-situ released hydrogen peroxide. The detection method incorporated into the present invention may be of the general type utilized in the clinical chemistry analysis of oxidase substrates which generate hydrogen peroxide. Hydrogen peroxide is usually allowed to oxidize a chromogen in the presence of an $H_2O_2$-decomposing enzyme, such as a peroxidase (POD), preferably isolated from horseradish. Peroxidase enzymes used in colorimetric reactions serve as catalysts for an oxidation reaction of a hydrogen donor by the hydrogen peroxide. Optimal enzyme activity is achieved at a defined pH for the specific enzyme, and is ensured via suitable buffers known in the art.

The chromogen may be chosen from two groups, leucodye type chromogens that oxidize to form color products; and coupling type chromogens that oxidize and then are coupled with a coexisting coupler to form a color product. The leucodye type chromogens include benzidine type compounds, diphenylamine, triarylmethane, 3-substituted imidazole type compounds and the like. Examples of leuco-dye type chromogen are 3,3',5,5'-tetramethylbenzidine; 2,2"-azino-di-(3-ethylbenzthiazoline)-6-sulfonate and 2-(4-hydroxy-3,5-dimethoxyphenyl)-4,5-bis(4-dimethylamino)phenyl imidazole. The coupling type chromogens includes phenazone and benzothiazolinone hydrazone type compounds, such as 4-aminoantipyrine and 3-methyl-2-benzothiazolinone hydrazone. The couplers include phenol, naphthol, aniline type compounds and primaquine, 3,5-dichloro-2-hydroxy-1-benzenesulfonic acid, chromotropic acid and primaquine diphosphate.

The enzyme and chromogen are preferably stabilized with protective binders, preferably hydrophilic polymers such as polyvinyl alcohol, polyvinylpyrrolidon, polyacrylates, gelatin, carboxymethyl cellulose, hydroxypropyl cellulose or hydroxypropyl methylcelulose, as known in the art.

Thus carrier 16 may contain such a peroxidase enzyme, such as horseradish peroxidase, along with TMB (3,3',5,5' tetramethylbenzidine), which in combination provide the a colormetric indicator for peroxide. The TMB acts as a proton donor for the decomposition of peroxide to water, oxidizing to a diamine form which yields a blue solution. Again, a solution of the reagents are prepared, the carrier dipped or other wise saturated with the solution, and allowed to dry.

With the carriers dry, they may be mounted onto the support member. Carrier 14 is shown affixed to the support member 12 along its entire length. Such affixation may be accomplished by use of double-sided tape or an appropriate adhesive, applied to either the support member 12 and/or the contacting surface of the carrier. Second carrier 16 may be affixed to the support member at a location above carrier 14 such that the carrier overlies at least a portion of the first carrier 14, ensuring that the reagents on carrier 16 effectively react with the results of the reaction between the reagent on carrier 14 and the initial solute.

While FIG. 1 depicts the two carriers separated from each other for clarity purposes, it is to be recognized that in use the two carriers will be in contact with each other, but as the components are inactive until they are dipped into the test solution, there is no interaction and the tester 10 may be stored in a dry environment for extended periods without degradation. It is recommended, however, that storage be in a tightly closed chamber or pouch with a desiccant to ensure that the tester is not degraded by environmental moisture.

To use the tester, the reagents on the carriers are activated with water, either by dipping the carrier-bearing end of the tester into a vial of water or by applying water to the carriers, such as by a dropper. After solubilization of the carried reagents the material to be tested is applied to the tester, either by dipping the tester into a solution of the material to be tested or by swabbing the carriers across the material. Any peroxide-based compound will decompose when contacted by the activated acid, releasing hydrogen peroxide as a direct analyte for a following colorimetric reaction, resulting in a detectable color change. When such color change is observed, the result of the test is positive indication of the presence of a hydrogen peroxide-based material, e.g. an explosive.

Figure 2:
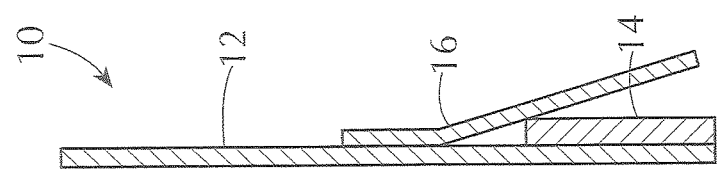

FIG. 2 presents an alternative embodiment of the tester construction, in which an end of the carrier 16 bearing the colorimetric indicators is affixed to a corresponding end portion of the underlying carrier 14 bearing the acid. In use this tester is activated and use in the same manner as the embodiment presented in FIG. 1. Once again, the distal ends of the carriers are shown displaced from each other solely for clarity purposes.

Figure 3:
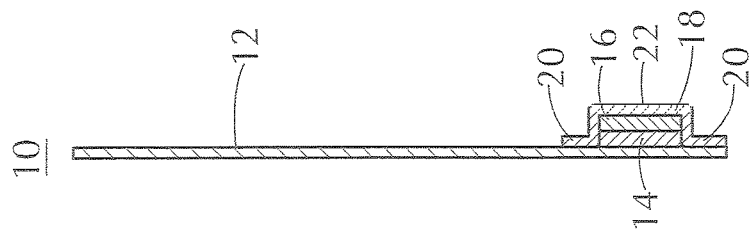
FIG. 3 is a side elevation representation embodiment similar to that of FIGS. 1 and 2 in which carrier components are covered.

FIGS. 3 through 7 present other alternative constructions for the present invention, intended for testing of solutions of suspected materials. With reference first to FIG. 3, carrier 14, bearing the acid, is mounted to support member 12 along its entire length, while second carrier 16, bearing the colorimetric indicators, lies upon the outer surface of carrier 14. The carrier pair is overlaid with a permeable transparent cover 18, isolating the carriers from physical contact with the ambient surroundings, while allowing solutions to pass through the cover into contact with the carriers. The edges 20 of the cover are affixed to the support member by an adhesive about the periphery of the cover. It is to be appreciated that the carriers need not be of equal size. And while it is preferred that the colorimetric indicator carrier 16 be directly under the cover, depending on the relative sizes of the carriers and the expected intensity and flow of the color-bearing composition, it may be possible to orient the carriers differently under the cover.

The tester is activated by dipping the carrier end into water, or applying water by a dropper to the cover. The water is permeates the cover, contacting the carriers and activating the reagents on the carriers. A solution of the sample to be tested is then applied to the tester, preferably by either dipping the tester end into the solution or by applying the solution to the tester through a dropper or other means. The test solution likewise passes through the permeable cover to contact the carriers and allow the indicator reactions to proceed. Any color change may be observed through the transparent cover. If full protection for the carriers is not desired, the cover 18 may be provided with a small aperture 22 to assist in rapid receipt of liquids by the carriers. In such a case, the cover 18 may be constructed of a non-permeable material. While use of a transparent material may still be preferable, if the aperture 22 is made sufficiently large to provide effective viewing of the underlying colormetric reaction, the cover may be non-transparent.

Figure 4:
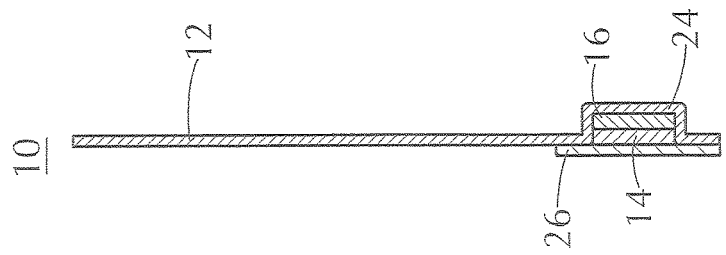
FIGS. 4 and 5 are respectively front and side elevation representations of an alternative embodiment of the invention.
Figure 5:
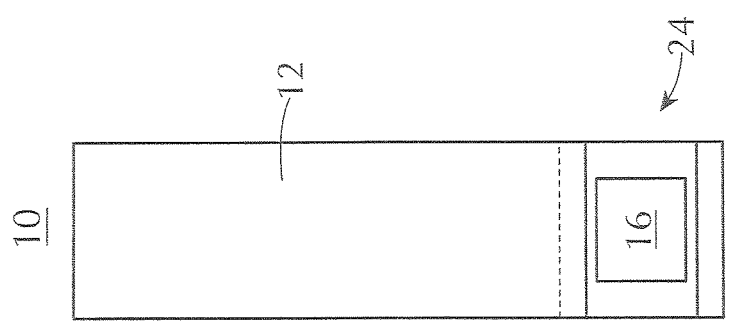

FIGS. 4 and 5 depicts an embodiment of the invention wherein the support member 12 is in the form of an elongated flat member of a transparent plastic with a molded depression or well 24 in which the carriers 14 and 16 are placed. The carriers are stacked in the well and are retained therein by permeable material 26 which completely covers the carriers and is adhered to the support member 12 to close off the well.

The carriers are activated, and a sample applied to the tester, in the manner similar to that for the previous embodiment, and the results of any colormetric reaction is observed through the transparent wall of the well.

Figure 6:
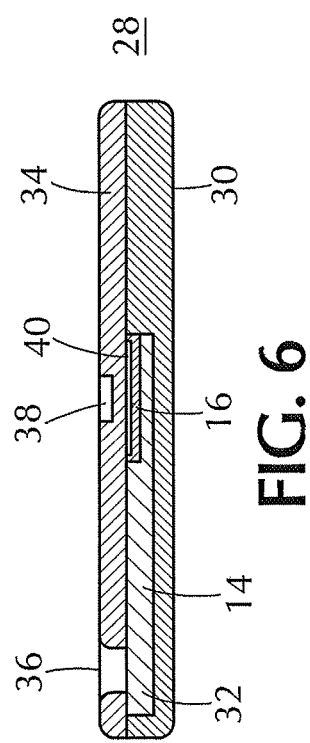
FIGS. 6 and 7 are respectively side and top view representations of yet another embodiment of the invention.
Figure 7:
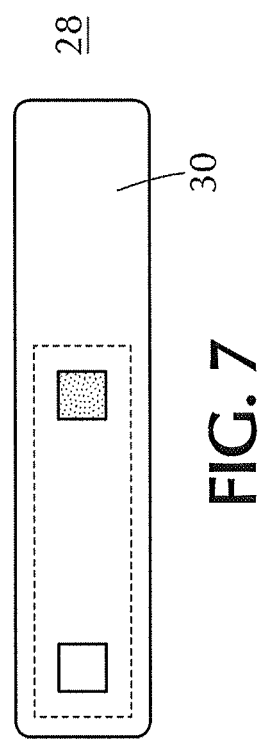

FIGS. 6 and 7 illustrate a further construction of the present invention in a plastic unit. As depicted, tester 28 may include a support member in the form of an elongated base 30 having well 32 therein at one end, the other end serving as a handle or grip portion for the tester. Cover 34 overlies the well. The cover has a fluid application aperture 36 and a viewing window 38. The carriers 14 and 16 are arranged in the well such that a solution to be tested is applied through the aperture 36 onto the first carrier 14 and is wicked through the carrier to second carrier 16 bearing the colormetric indicators. As depicted, the carrier 14 may extend along the entire length of the well, and is overlaid with the second carrier 16 in an area below the viewing aperture 38. A transparent element, such as transparent foil 40, may close the lower end of the viewing aperture 38.

After activation of the carriers by wetting through the receiving aperture 36, a solution of the material to be tested is likewise applied through aperture 36 onto the first carrier and is wicked through the first carrier to the second carrier placed directly under the viewing window. Any color change is observable through the window.

We claim:

1. An apparatus for the colorimetric detection testing of peroxide-based compositions, comprising:
    an acidic compound in dry form for hydrolysis of peroxide-based compounds;
    a first dry carrier in the form of an absorbent/adsorbent substrate for the acidic compound;
    a peroxide-sensitive colorimetric detection reagent composition in dry form;
    a second dry carrier in the form of an absorbent/adsorbent substrate for the reagent composition; and
    a support member for the first and second carriers;
    the carriers being positioned with respect to the support member to facilitate transfer of a resulting solution containing a peroxide-based compound hydrolyzed by the acidic compound when the acidic compound is activated by wetting into contact with the colorimetric detection reagent composition of the second carrier for observation of any resulting color indication.

2. The apparatus of claim 1 wherein the first and second carriers are positioned on the support member with their carried compositions in intimate contact with each other.

3. The apparatus of claim 2 wherein a portion of the second carrier overlies the first carrier.

4. The apparatus of claim 1 wherein the support member is of an elongated construction, the carriers being positioned on the support member proximate a first end thereof, a second end of the support member serving as a handle for the apparatus.

5. The apparatus of claim 1 wherein the carriers are at least partially enclosed within a permeable covering.

6. The apparatus of claim 5 wherein the permeable covering is affixed to a portion of the support member about covering edges, the covering and a portion of the support member together forming a housing for the carriers.

7. The apparatus of claim 6 wherein the permeable member is transparent, and the second carrier is positioned adjacent the permeable member.

8. The apparatus of claim 6 wherein the support member has a well for receipt of the carriers, the well having an opening covered by the permeable member.

9. The apparatus of claim 8 wherein the well is molded into the support member.

10. The apparatus of claim 1 wherein the support member comprises a plate with a recess for the carriers and a cover overlying the recess, the carrier having a first aperture for receiving a sample solution to be tested and a second aperture for observation of the color indication.

11. The apparatus of claim 10, wherein the carriers are positioned in the recess whereby the first aperture overlies a portion of the first carrier and the second aperture overlies a portion of the second carrier.

12. The apparatus of claim 11 wherein the second aperture is closed by a transparent layer.

13. A method for the colorimetric determination of the presence of a peroxide based compound in a sample, comprising the steps of:
    applying a solution of an acidic compound to a first carrier and allowing the solution to dry whereby the acidic compound remains in dry form on the first carrier;
    applying a solution of a peroxide-sensitive colorimetric detection reagent composition to a second carrier and allowing the solution to dry whereby the reagent composition remains in dry form on the second carrier;
    mounting the first and second carriers to a support member in a manner to facilitate transfer of a solution containing a peroxide-based compound hydrolyzed by the acidic compound when activated into contact with the reagent composition on the second carrier for observation of any color indication;
    activating the acidic compound and reagent composition on the carriers by wetting;
    contacting the sample to the first carrier; and
    observing the reagent composition for a color change.

14. The method of claim 13 wherein the wetting step is performed by dipping the carriers into a liquid.

* * * * *